United States Patent [19]
Colacino et al.

[11] Patent Number: 5,821,242
[45] Date of Patent: Oct. 13, 1998

[54] ANTI-VIRAL COMPOUNDS

[75] Inventors: Joseph Matthew Colacino, Indianapolis; Beverly Ann Heinz, Bargersville; Louis Nickolaus Jungheim, Indianapolis; Shawn Christopher Miller, Indianapolis; Wayne Alfred Spitzer, Indianapolis; Joseph Chiou-chung Tang, Carmel; Mark Joseph Tebbe; Frantz Victor, both of Indianapolis, all of Ind.

[73] Assignee: Eli Lilly and Company, Indianapolis, Ind.

[21] Appl. No.: 868,638

[22] Filed: Jun. 4, 1997

Related U.S. Application Data

[60] Provisional application No. 60/019,224 Jun. 6, 1996.

[51] Int. Cl.$^6$ ............... C07D 235/22; C07D 235/08; A61K 31/415
[52] U.S. Cl. ............... 514/227.2; 514/234.5; 514/322; 514/395; 544/55; 544/116; 546/199; 548/306.1; 548/304.1; 548/307.1
[58] Field of Search ............... 514/227.2, 234.5, 514/322, 395; 544/55, 46; 546/199; 548/306.1, 304.1, 307.1

[56] References Cited

U.S. PATENT DOCUMENTS

| 4,401,817 | 8/1983 | Paget et al. | 548/136 |
| 4,420,479 | 12/1983 | Morwick et al. | 514/227.2 |
| 4,434,288 | 2/1984 | Wikel | 544/54 |
| 4,492,708 | 1/1985 | Spitzer | 514/394 |
| 5,216,003 | 6/1993 | Vazquez | 514/381 |
| 5,545,653 | 8/1996 | Miller et al. | 514/388 |

OTHER PUBLICATIONS

CA 100:139101, abstract of EP 91794, Oct. 19, 1983.
WPIDS 83–796734, abstract of EP 91794, Oct. 19, 1984, with equivalent world patent listing.
CAS Search reports of EP 91794, Oct. 19, 1983.
CAS Search results of JP58188868, Nov. 4, 1983.
CAS Search report of DD 207714, Mar. 14, 1984.

*Primary Examiner*—John Kight
*Assistant Examiner*—D. Margaret M. Mach
*Attorney, Agent, or Firm*—Janet T. McClain; David E. Boone

[57] ABSTRACT

The present application provides a series of benzimidazole compounds which inhibit the growth of picornaviruses, such as rhinoviruses, enteroviruses, polioviruses, coxsackieviruses of the A and B groups, echo virus and Mengo virus and flaviviruses such as hepatitis C and bovine diarrheal virus.

14 Claims, No Drawings

ANTI-VIRAL COMPOUNDS

This application claims priorty to Provisional application Ser. No. 60/019,22 filed 6 Jun. 1996.

FIELD OF THE INVENTION

The present invention is in the field of human medicine, particularly in the treatment of viral infections. More particularly, the present invention relates to the treatment of rhinoviral, enteroviral and flaviviral inventions.

BACKGROUND OF THE INVENTION

The incidence of viral upper respiratory disease, the common cold, is immense. It has been estimated that nearly a billion cases annually appear in the United States alone. Rhinovirus, a member of the picornaviridae family, is the major cause of the common cold in humans. Because more than 110 strains of rhinoviruses have been identified, the development of a practical rhinovirus vaccine is not feasible, and chemotherapy appears to be the more desirable approach. Another member of the picornavirus family is the enterovirus, which includes approximately eighty human pathogens. Many of these enteroviruses cause cold-like symptoms; others can cause more serious diseases such as polio, conjunctivitis, aseptic meningitis and myocarditis.

Illness related to rhinovirus infection is evidenced by nasal discharge and obstruction Furthermore, it has been implicated in otitis media, predisposes the development of bronchitis, exacerbates sinusitis, and has been implicated in the precipitation of asthmatic altoclis. Although it is considered by many to be a mere nuisance, its frequent occurrence in otherwise healthy individuals and the resulting economic importance in terms of employee absenteeism and physician visits have made it the subject of extensive investigation.

The ability of chemical compounds to suppress the growth of viruses in vitro may be readily demonstrated using a virus plaque suppression test or a cytopathic effect test (CPE). Cf Siminoff, Applied Microbiology, 9(1), 66 (1961). Although a number of chemical compounds that inhibit picornaviruses such as rhinoviruses have been identified, many are unacceptable due to 1) limited spectrum of activity, 2) undesirable side effects or 3) inability to prevent infection or illness in animals or humans. See *Textbook of Human Virology*, edited by Robert B. Belshe, chapter 16, "Rhinoviruses," Roland A. Levandowski, 391–405 (1985). Thus, despite the recognized therapeutic potential associated with a rhinovirus inhibitor and the research efforts expended thus far, a viable therapeutic agent has not yet emerged. For example, anti-viral benzimidazole compounds have been disclosed in U.S. Pat. Nos. 4,008,243, 4,018,790, 4,118,573, 4,118,742, 4,174,454 and 4,492,708.

In general, the compounds disclosed in the above patents do not have a desirable pharmacological profile for use in treating rhinoviral infections. Specifically, these compounds do not possess satisfactory oral bioavailability or a high enough inhibitory activity to compensate for their relatively low oral bioavailability to permit their widespread use. In addition, it is widely accepted in the art that compounds used to treat rhinoviral infections should be very safe from a toxicological standpoint.

SUMMARY OF THE INVENTION

Accordingly, it is a primary object of this invention to provide novel benzimidazole compounds which inhibit the growth of picornaviruses, such as rhinoviruses, enteroviruses such as polioviruses, coxsackieviruses of the A and B groups, or echo virus and which have a desirable pharmacological profile. The benzimidazole compounds may also be used to inhibit flaviviruses such as hepatitis C and bovine diarrheal virus (BVDV).

The present invention provides compounds of formula I

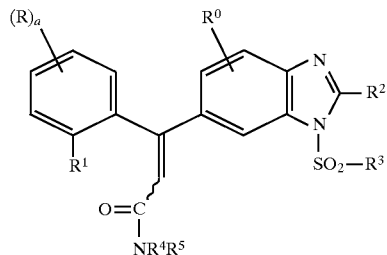

wherein:
a is 0, 1, 2 or 3;
each R is independently hydrogen, halo, cyano, amino, halo($C_1$–$C_4$)alkyl, di($C_1$–$C_4$)alkylamino, azido, $C_1$–$C_6$ alkyl, carbamoyl, carbamoyloxy; carbamoylamino, $C_1$–$C_4$ alkoxy, $C_1$–$C_4$ alkylthio, $C_1$–$C_4$ alkylsulfinyl, $C_1$–$C_4$ alkylsulfonyl, pyrrolidino, piperidino or morpholino;
$R^0$ is hydrogen, halo, $C_1$–$C_4$ alkyl or $C_1$–$C_4$ alkoxy;
$R^1$ is halo, cyano, hydroxy, methyl, ethyl, methoxy, ethoxy, methylthio, methylsulfinyl or methylsulfonyl;
$R^2$ is hydrogen, amino or —NHC(O)($C_1$–$C_6$ alkyl);
$R^3$ is dimethylamino, $C_1$–$C_{10}$ alkyl, halo($C_1$–$C_6$)alkyl, $C_3$–$C_7$ cycloalkyl, substituted $C_3$–$C_7$ cycloalkyl, phenyl, substituted phenyl, naphthyl, thienyl, thiazolidinyl, furyl, pyrrolidino, piperidino, morpholino or a group of the formula:

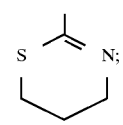

$R^4$ and $R^5$ are independently hydrogen or $C_1$–$C_4$ alkyl; or a pharmaceutically acceptable salt thereof.

The present invention also provides pharmaceutical formulations comprising a compound of the present invention, or a pharmaceutically acceptable salt thereof, in combination with a pharmaceutically acceptable carrier, diluent or excipient therefor.

The present invention also provides a method for inhibiting a picornavirus comprising administering to a host in need thereof, an effective amount of a compound of formula I, or a pharmaceutically acceptable salt thereof, wherein a, R, $R^0$, $R^1$, $R^2$, $R^3$, $R^4$ and $R^5$ are as defined above.

DETAILED DESCRIPTION

The present invention relates to benzimidazole compounds of formula I, as described above, that are useful as antiviral agents.

All temperatures stated herein are in degrees Celsius (°C.). All units of measurement employed herein are in weight units except for liquids which are in volume units.

As used herein, the term "$C_1$–$C_{10}$ alkyl" represents a straight or branched alkyl chain having from one to ten carbon atoms. Typical $C_1$–$C_{10}$ alkyl groups include methyl, ethyl, propyl, isopropyl, butyl, isobutyl, sec-butyl, t-butyl, pentyl, neo-pentyl, hexyl, 2-methylhexyl, heptyl and the like. The term "$C_1$–$C_{10}$ alkyl" includes within its definition the terms "$C_1$–$C_6$ alkyl" and "$C_1$–$C_4$ alkyl."

"Halo" represents chloro, fluoro, bromo or iodo.

"Halo($C_1$–$C_4$)alkyl" represents a straight or branched alkyl chain having from one to four carbon atoms with 1, 2 or 3 halogen atoms attached to it. Typical halo($C_1$–$C_4$)alkyl groups include chloromethyl, 2-bromoethyl, 1-chloroisopropyl, 3-fluoropropyl, 3-bromobutyl, 3-chloroisobutyl, iodo-t-butyl, trichloromethyl, trifluoromethyl, 2,2-chloro-iodoethyl, 2,3-dibromopropyl and the like.

"$C_1$–$C_4$ alkylthio" represents a straight or branched alkyl chain having from one to four carbon atoms attached to a sulfur atom. Typical $C_1$–$C_4$ alkylthio groups include methylthio, ethylthio, propylthio, isopropylthio, butylthio and the like.

"$C_1$–$C_4$ alkoxy" represents a straight or branched alkyl chain having from one to four carbon atoms attached to an oxygen atom. Typical $C_1$–$C_4$ alkoxy groups include methoxy, ethoxy, propoxy, isopropoxy, butoxy and the like.

"Di($C_1$–$C_4$)alkylamino" represents two straight or branched alkyl chains having from one to four carbon atoms attached to a common amino group. Typical di($C_1$–$C_4$) alkylamino groups include dimethylamino, ethylmethylamino, methylpropylamino, ethylisopropylamino, butylmethylamino, sec-butylethylamino and the like.

"$C_1$–$C_4$ alkylsulfinyl" represents a straight or branched alkyl chain having from one to four carbon atoms attached to a sulfinyl moiety. Typical $C_1$–$C_4$ alkylsulfinyl groups include methylsulfinyl, ethylsulfinyl, propyl-sulfinyl, isopropyl-sulfinyl, butylsulfinyl and the like.

"$C_1$–$C_4$ alkylsulfonyl" represents a straight or branched alkyl chain having from one to four carbon atoms attached to a sulfonyl moiety. Typical $C_1$–$C_4$ alkylsulfonyl groups include methylsulfonyl, ethylsulfonyl, propylsulfonyl, isopropyl-sulfonyl, butylsulfonyl and the like.

"Substituted phenyl" represents a phenyl ring substituted with 1–3 substituents selected from the following: halo, cyano, $C_1$–$C_4$ alkyl, $C_1$–$C_4$ alkoxy, amino or halo($C_1$–$C_4$) alkyl.

"Substituted $C_3$–$C_7$ cycloalkyl" represents a cycloalkyl ring substituted with 1–3 substituents selected from the following: halo, cyano, $C_1$–$C_4$ alkyl, $C_1$–$C_4$ alkoxy, amino or halo ($C_1$–$C_4$) alkyl.

The claimed compounds can occur in either the cis or trans isomer. For the purposes of the present application, cis refers to those compounds where the carboxamide moiety is cis to the benzimidazole ring and trans refers to those compounds where the carboxamide moiety is trans to the benzimidazole ring. Both isomers are included in the scope of the claimed compounds.

As mentioned above, the invention includes the pharmaceutically acceptable salts of the compounds defined by formula I. A compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methane-sulfonic acid, ethanesulfonic acid, oxalic acid, p-bromophenylsulfonic acid, carbonic acid, succinic acid, citric acid, benzoic acid, acetic acid and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, ethanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and sulfuric acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of this invention are those compounds of the formula:

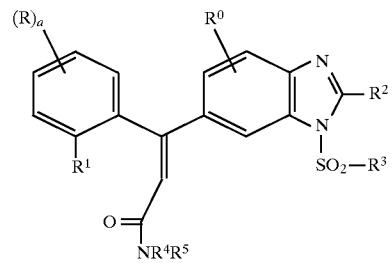

where:

a is 0, 1 or 2;

each R is independently hydrogen, halo, $C_1$–$C_4$ alkyl, $C_1$–$C_4$ alkoxy or di($C_1$–$C_4$)alkylamino;

$R^0$ is hydrogen;

$R^2$ is amino;

$R^3$ is dimethylamino, $C_1$–$C_6$ alkyl, halo($C_1$–$C_6$)alkyl, $C_3$–$C_7$ cycloalkyl, substituted $C_3$–$C_7$ cycloalkyl, thienyl, thiazolidinyl, pyrrolidino, piperidino or morpholino;

$R^4$ is hydrogen, methyl or ethyl;

$R^5$ is hydrogen, methyl or ethyl;

or a pharmaceutically acceptable salt thereof.

Of these preferred compounds, more preferred are those compounds of formula I where:

a is 0 or 1;

each R is independently hydrogen, fluoro, methyl, ethyl, methoxy, ethoxy, dimethylamino;

$R^0$ is hydrogen;

$R^3$ is dimethylamino, $C_1$–$C_4$ alkyl, $C_3$–$C_7$ cycloalkyl or pyrrolidino;

or a pharmaceutically acceptable salt thereof.

Of these compounds, the most preferred compounds are:

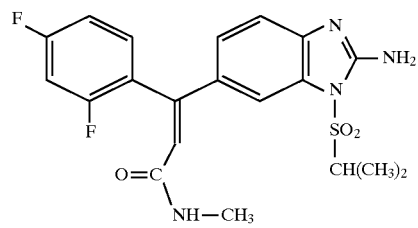

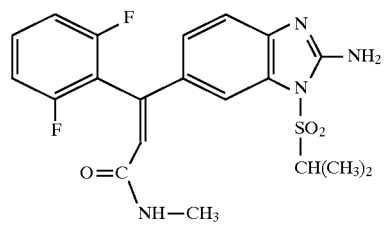

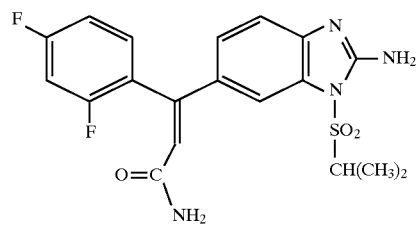

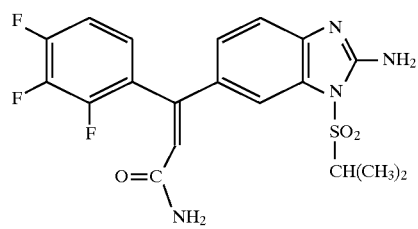

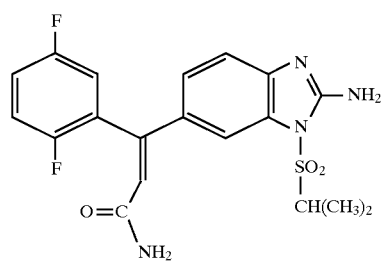

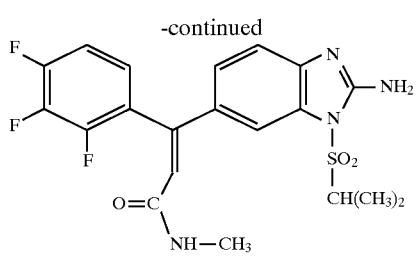

or a pharmaceutically acceptable salt thereof.

The compounds of formula I may be prepared by reacting a suitably substituted acetamide with a base to provide the corresponding anion which is then reacted with a suitably substituted ketone of formula IA to provide a carbinol intermediate. The reactions are typically carried out in an organic solvent for one to twelve hours at a temperature of from about –90° C. to room temperature using an excess of the base and acetamide reactant relative to the ketone reactant. The acetamide is preferably protected with a suitable protecting group prior to use in the reaction. Typical bases include sodium hydride, lithium diisopropylamide (LDA) and n-butyllithium. A preferred base is n-butyllithium. Solvent choice is not critical so long as the solvent employed is inert to the ongoing reaction and the reactants are sufficiently solubilized to effect the desired reaction. A solvent that is suitable for use in this reaction is tetrahydrofuran although the acetamide reactant can also be used as a solvent. The carbinol intermediate is generally prepared in from about one to eighteen hours when the reaction is initiated at –78° C. and allowed to slowly warm to room temperature. The reaction may be monitored by HPLC and quenched by the addition of an acid when it is substantially complete. Typical acids include hydrochloric acid, hydrobromic acid, formic acid and the like. A preferred acid is concentrated hydrochloric acid. The resultant carbinol intermediate is preferably dehydrated without prior isolation or purification.

In particular, the carbinol intermediate is reacted with an acid for thirty minutes to twelve hours at a temperature of from about room temperature to the reflux temperature of the mixture to provide the desired compound of formula I. Typical acids include hydrochloric acid, hydrobromic acid, formic acid, acetic acid and combinations of acids. A preferred acid combination is formic acid containing 1–6% concentrated hydrochloric acid. The desired compound is generally prepared in from about thirty minutes to seven hours when the reaction is carried out at the reflux temperature of the mixture. The reaction is preferably monitored by HPLC, for example, to ensure that the reaction goes to completion.

The compounds of formula I are preferably isolated and the resulting cis/trans isomers separated using procedures known in the art. For example, the cis and trans forms of the isolated compounds may be separated using column chromatography, for example reverse phase HPLC. The compounds may be eluted from the column using an appropriate ratio of acetonitrile and water or methanol and water. The cis form of the compound may be converted to a cis/trans mixture by exposure to hv irradiation and recycled through the above-mentioned purification process.

The ketone intermediates of formula IA used in the above reaction may be prepared substantially as detailed in the art. For example, the ketone intermediates may be prepared according to the following Reaction Scheme I.

Reaction Scheme I

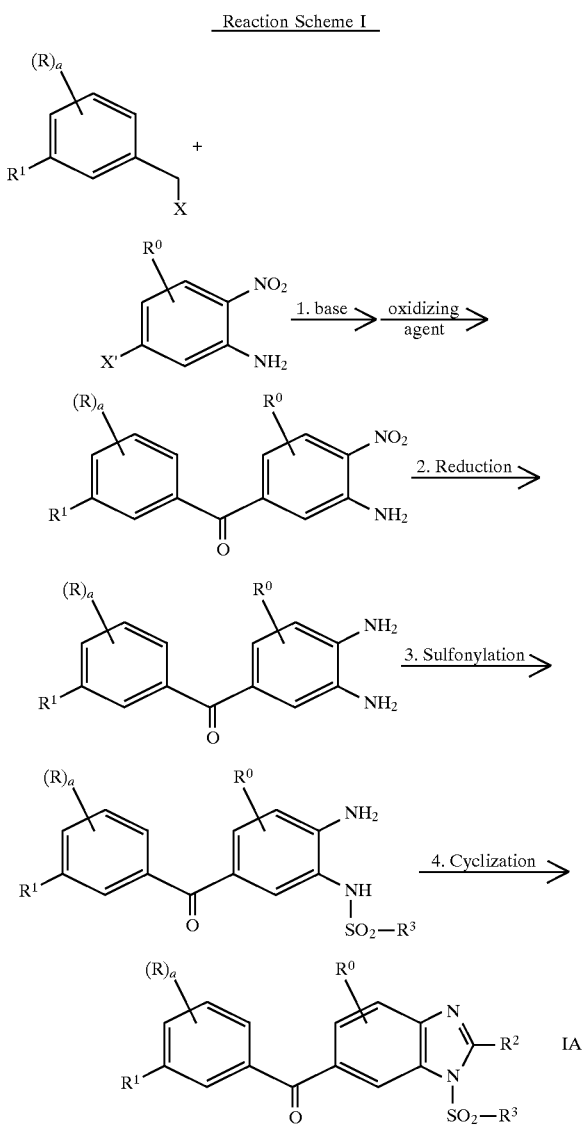

where:

X is cyano or —COOR', where R' is $C_1$–$C_4$ alkyl;

X' is halo; and a, R, $R^0$, $R^1$, $R^2$ and $R^3$ are defined above.

Reaction Scheme I, above, is accomplished by carrying out reactions 1–4. Once a reaction is complete, the intermediate compound may be isolated, if desired, by procedures known in the art. For example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

Reaction I.1 is accomplished by first exposing an appropriately substituted halo-nitroaniline, preferably fluoro- or chloro-nitroaniline and an appropriately substituted phenylacetonitrile or benzoate to a base in an organic solvent for one to twenty four hours at a temperature of from about –10° C. to about 40° C. to provide a ketone precursor. The reaction is typically carried out using equimolar proportions of the reactants in the presence of two equivalents of the base. Typical bases include sodium hydride, potassium t-butoxide, lithium diisopropylamide (LDA). A preferred base is potassium t-butoxide. Examples of solvents suitable for use in this reaction include dimethylformamide, dimethylacetamide and the like. Solvent choice is not critical so long as the solvent employed is inert to the ongoing reaction and the reactants are sufficiently solubilized to effect the desired reaction. The ketone precursor is generally prepared in from about one to fifteen hours when the reaction is initiated at 0° C. and allowed to progress at room temperature. The ketone precursor is preferably oxidized in the same reaction mixture without prior isolation or purification.

In particular, the ketone precursor is reacted with an oxidizing agent for thirty minutes to fifteen hours at a temperature of from about 0° C. to about 30° C. to provide the corresponding ketone compound. Typical oxidizing agents include hydrogen peroxide, oxygen and air. The oxygen and air are typically bubbled through the reaction mixture. A preferred oxidizing agent is hydrogen peroxide, preferably in a 30% solution. The ketone is generally prepared in from about thirty to five hours when the reaction is carried out between 0° C. and room temperature. The reaction is preferably monitored by TLC, for example, to ensure that the reaction goes to completion.

In reaction I.2, the nitro substituent on the ketone is reduced according to procedures known in the art to provide the corresponding diaminobenzophenone compound. For example, the nitro substituent may be reduced by catalytic hydrogenation, for example by combining the ketone isolated from reaction II.1 with hydrogen gas in ethanol or tetrahydrofuran and a catalyst. A preferred catalyst is palladium-on-carbon or Raney nickel. Solvent choice is not critical so long as the solvent employed is inert to the ongoing reaction and the nitro reactant is sufficiently solubilized to effect the desired reaction. The hydrogen gas is typically used at a pressure of up to 60 psi, preferably at or about 30 psi. The reaction is generally substantially complete after about 1 to 24 hours when conducted at a temperature in the range of from about 0° C. to about 40° C. The reaction is preferably conducted at a temperature in the range of from about 20° C. to about 30° C. for about 2 to 5 hours.

In reaction I.3, the diaminobenzophenone compound isolated from reaction I.2 may be sulfonylated with an appropriately substituted sulfonyl halide of the formula $R^4$-$SO_2$-halide substantially in accordance with the procedure detailed above to provide the corresponding sulfonamido benzophenone compounds.

In reaction I.4, the compound isolated from reaction I.3 is cyclized via a nitrile intermediate by first exposing the sulfonamido benzophenone compound to a base in an alcoholic solvent such as isopropanol followed by reaction with cyanogen bromide. Typically, the sulfonamido benzophenone and base are reacted at a temperature of from about 0° C. to about 30° C. A preferred base is sodium hydroxide, preferably added in the form of an aqueous solution (about 1–4M). When the sulfonamido benzophenone is completely dissolved, the resultant solution is combined with cyanogen bromide. The cyanogen bromide is typically added in the form of a solution (3–7M for example in acetonitrile). The reaction is generally complete after one to eighteen hours when the reaction mixture is stirred at room temperature. However, in certain instances nitrile intermediate will precipitate out of the reaction mixture. In order to form the desired ketone, this precipitate is isolated and then refluxed in an alcoholic solvent such as isopropanol for one to four hours to provide the desired ketone compound of formula I.

Alternatively, the compound isolated from reaction I.3 is cyclized via a nitrile intermediate by exposing the sulfonamido benzophenone compound to a base in a chlorinated solvent such as methylene chloride followed by reaction with cyanogen bromide. Typically, the sulfonamido benzophenone and base are reacted at a temperature of from about 0° C. to about the reflux temperature of the mixture. A preferred base is lithium methoxide. The sulfonamido benzophenone and the base typically form a slurry which is then combined with cyanogen bromide. The cyanogen bromide is typically added in the form of a solution (3–7$\underline{M}$ for example in methylene chloride). The reaction is generally complete after one to eighteen hours when the reaction mixture is stirred at a temperature range of 0° C. to the reflux temperature.

The compounds of formula I where $R^2$ is —NHC(O) ($C_1$–$C_6$ alkyl) may be prepared by acylating a compound of formula I, where $R^2$ is amino, according to procedures known in the art. For example, the amine compound may be acylated with a suitable acyl halide, isocyanate or chloroformate, preferably in the presence of an acid scavenger such as a tertiary amine, preferably triethylamine. A preferred acylating agent is acetic anhydride. The reaction is typically carried out at a temperature of from about −20° C. to about 25° C. Typical solvents for this reaction include ethers and chlorinated hydrocarbons, preferably diethylether, chloroform or methylene chloride. The amine reactant is generally employed in equimolar proportions relative to the acylating reactant, and preferably in the presence of equimolar quantities of an acid scavenger such as a tertiary amine. A preferred acid scavenger for this reaction is N-methylmorpholine (NMM).

The compounds employed as initial starting materials in the synthesis of the compounds of this invention are known in the art, and, to the extent not commercially available are readily synthesized by standard procedures commonly employed in the art.

It will be understood by those in the art that in performing the processes described above it may be desirable to introduce chemical protecting groups into the reactants in order to prevent secondary reactions from taking place. Any amine, alcohol, alkylamine or carboxy groups which may be present on the reactants may be protected using any standard amino-, alcohol or carboxy-protecting group which does not adversely affect the remainder of the molecule's ability to react in the manner desired. The various protective groups may then be removed simultaneously or successively using methods known in the art.

The pharmaceutically acceptable salts of the invention are typically formed by reacting a compound of formula I with an equimolar or excess amount of acid or base. The reactants are generally combined in a mutual solvent such as diethylether, tetrahydrofuran, methanol, ethanol, isopropanol, benzene and the like, for acid addition salts, or water, an alcohol or a chlorinated solvent such as methylene chloride for base addition salts. The salts normally precipitate out of solution within about one hour to about ten days and can be isolated by filtration or other conventional methods.

The following Preparations and Examples further illustrate specific aspects of the present invention. It is to be understood, however, that these examples are included for illustrative purposes only and are not intended to limit the scope of the invention in any respect and should not be so construed.

In the following Preparations and Examples, the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are abbreviated "m.p.", "NMR", "EIMS", "MS(FD)", "MS(FAB)", "IR", "UV", "Analysis", "HPLC", and "TLC", respectively. The MS(FD) data is presented as the mass number unless otherwise indicated. In addition, the absorption maxima listed for the IR spectra are only those of interest and not all of the maxima observed.

In conjunction with the NMR spectra, the following abbreviations are used: "s" is singlet, "d" is doublet, "dd" is doublet of doublets, "t" is triplet, "q" is quartet, "m" is multiplet, "dm" is a doublet of multiplets and "br.s", "br.d", "br.t", and "br.m" are broad singlet, doublet, triplet, and multiplet respectively. "J" indicates the coupling constant in Hertz (Hz). Unless otherwise noted, NMR data refers to the free base of the subject compound.

The NMR spectra were obtained on a Brüker Corp. 250 MHz instrument or on a General Electric QE-300 300 MHz instrument. The chemical shifts are expressed in delta, δ values (parts per million downfield from tetramethylsilane). The MS(FD) spectra were taken on a Varion-MAT 731 Spectrometer using carbon dendrite emitters. EIMS spectra were obtained on a CEC 21-110 instrument from Consolidated Electrodynamics Corporation. IR spectra were obtained on a Perkin-Elmer 281 instrument. UV spectra were obtained on a Cary 118 instrument. TLC was carried out on E. Merck silica gel plates. Melting points are uncorrected.

EXAMPLE 1

A. 3-Amino-4-nitro-4'-fluorobenzophenone

To a cold (0° C.) solution of 17.25 g (100 mmol) of 5-chloro-2-nitroaniline and 12 ml (100 mmol) of 4-fluorophenylacetonitrile in 200 ml of dimethylformamide, was added 22.44 g (200 mmol) of potassium t-butoxide, under nitrogen. The reaction mixture was warmed to room temperature and reacted overnight. When the reaction was substantially complete, as indicated by TLC (eluent of 40% ethyl acetate in hexane), the reaction mixture was cooled to 0° C. followed by the addition of 30 ml of hydrogen peroxide (30% solution in water). When the reaction was substantially complete, as indicated by TLC (eluent of 40% ethyl acetate in hexane), the reaction mixture was poured into 1 liter of 1N hydrochloric acid (aqueous) which resulted in the formation of a yellow/orange precipitate.

This precipitate was isolated by filtration. Yield: 23.3 g (89%).

B. 3,4-Diamino-4'-fluorobenzophenone

To a solution of 21 g of Example 1A in 250 ml of tetrahydrofuran and 250 ml of ethanol, was added 3.0 g of Raney Nickel catalyst. The reaction mixture was stirred overnight under 30 psi of hydrogen (gas) and then filtered. The filtrate was concentrated in vacuo to provide a yellow solid which was used without further purification.

C. 4-Amino-3-isopropylsulfonamido-4'-fluorobenzophenone

To a solution of 18.14 g (79 mmol) of Example 1B in 160 ml of anhydrous methylene chloride and 32 ml of anhydrous pyridine, was added 13.25 ml (118 mmol) of isopropylsulfonylchloride. The reaction mixture was reacted at room temperature for 5 hours, under nitrogen. When the reaction was substantially complete, as indicated by TLC (eluent of ethyl acetate), the reaction mixture was poured into 400 ml of 1N hydrochloric acid (aqueous). The resulting mixture was diluted with 300 ml of ethyl acetate and the resulting layers were separated, the organic layer dried over magnesium sulfate, filtered and concentrated in vacuo to provide a dark red gum. This gum was purified using Preparatory HPLC (gradient eluent of 30–60% ethyl acetate in hexane). The fractions containing the desired compound were combined and dried in vacuo to provide 17.11 g of a yellow gum that was used without further purification. Yield: 65%

D. 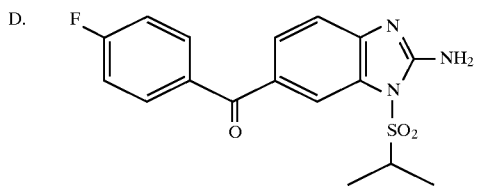

To a solution of 17.11 g (51 mmol) of Example 1C and 25 ml of 2N sodium hydroxide (aqueous) in 100 ml of isopropanol, was added 10 ml of a 5M cyanogen bromide in acetonitrile. The reaction mixture was reacted at room temperature for 30 minutes resulting in the formation of a precipitate. This precipitate was isolated by filtration to provide 11.68 g of a solid. This solid was resuspended in 250 ml of isopropanol and the resultant mixture was refluxed until all of the material had dissolved and then cooled to provide 10.0 g of the desired compound.

Yield: 55%.

Analysis for $C_{17}H_{16}FN_3O_3S$: Calcd: C, 56.50; H, 4.46; N, 11.63; Found: C, 56.71; H, 4.48; N, 11.82.

MS(FD): 361.

$^1$H NMR (300 MHz; $d_6$-DMSO): δ 1.32 (d, J=7 Hz, 6H); 3.96 (septet, J=7.0 Hz, 1H); 7.34–7.44 (m, 5H); 7.63 (dd, J=1.6,8.3 Hz, 1H); 7.79–7.83 (m, 2H); 7.95 (d, J=1.5 Hz, 1H).

E. 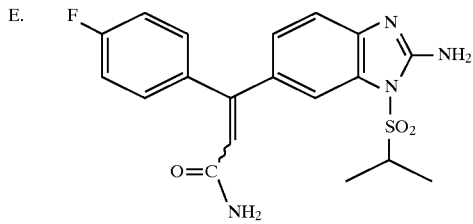

To a cold (−78° C.) solution of bis(trimethylsilyl) acetamide (8 equivalents) in tetrahydrofuran, was slowly added a solution of 2.5M n-butyllithium (8 equivalents) in hexane. To the resultant mixture was added Example 1D (1 equivalent). The reaction mixture was stirred for 8 hours at −78° C. and then allowed to warm to room temperature. When the reaction was substantially complete, as indicated by HPLC, the reaction was quenched by the addition of concentrated hydrochloric acid (approximately 1 equivalent) and then concentrated in vacuo to provide an oil which was then redissolved in formic acid containing 1% concentrated hydrochloric acid. The resultant mixture was allowed to react for 4 hours at 95° C. When the reaction was substantially complete, as indicated by HPLC, the mixture was concentrated in vacuo to provide an oil. This oil was separated using reverse phase HPLC (eluent of acetonitrile in water) to provide the cis and trans isomers.

cis not characterized trans

Analysis for $C_{19}H_{19}N_4O_3SF$: Calcd: C, 56.71; H, 4.76; N, 13.92; S, 7.97; F, 4.72; Found: C, 56.96; H, 4.76; N, 13.90; S, 7.96; F, 4.90.

MS(FD): 402 (M$^+$).

$^1$H NMR (300 MHz; $d_6$-DMSO): δ 1.20 (d, 6H); 3.80 (m, 1H); 6.35 (s, 1H); and 7.10 (m, 11H).

IR (CHCl$_3$): ν 3465, 3140, 1680, 1658, 1600, 1554, 1395, 1353, 1265, 1216, 1157, 1139, 1047, 689, 593 and 425 cm$^{-1}$.

UV/VIS (95% EtOH): $\lambda_{max}$=312.50 nm (E=15680.556); 245.00 nm (E=26956.305).

The compounds described in Examples 2–4 were prepared substantially as detailed in Example 1A–E, using N-methyl-N-trimethylsilylacetamide instead of bis (trimethylsilyl)acetamide.

EXAMPLE 2

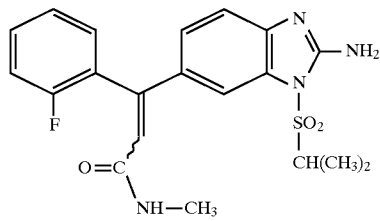

cis

Analysis for $C_{20}H_{21}N_4O_3SF$: Calcd: C, 57.68; H, 5.08; N, 13.45; Found: C, 57.69; H, 5.07; N, 13.36.

MS(FD): 416 (M$^+$)

$^1$H NMR (300 MHz; $d_6$-DMSO): δ 1.23 (d, J=7 Hz, 6H); 2.59 (d, J=5 Hz, 3H); 3.86 (septet, J=7 Hz, 1H); 6.13 (s, 1H); 6.85 (dd, J=8,1 Hz, 1H); 7.07 (s, 2H); 7.08–7.31 (m, 4H); 7.32–7.50 (m, 2H) and 8.01 (d, J=5 Hz, 1H).

IR (CHCl$_3$): ν 3450, 3410, 3350, 2996, 1659, 1639, 1608, 1548, 1359 and 1155 cm$^{-1}$.

UV/VIS (95% EtOH): $\lambda_{max}$=296.0 nm (E=12272); 252.0 nm (E=21329).

trans

Analysis for $C_{20}H_{21}N_4O_3SF$: Calcd: C, 57.68; H, 5.08; N, 13.45; Found: C, 57.91; H, 5.07; N, 13.47.

MS(FD): 416 (M$^+$).

$^1$H NMR (300 MHz; $d_6$-DMSO): δ 1.25 (d, J=7 Hz, 6H); 2.59 (d, J=5 Hz, 3H); 3.82 (septet, J=7 Hz, 1H); 6.58 (s, 1H); 7.04 (dd, J=8,1 Hz, 1H); 7.14–7.21 (m, 6H); 7.37–7.42 (m, 2H) and 8.01 (d, J=5 Hz, 1H).

IR(CHCl$_3$): ν 3460, 3310, 2990, 1639, 1603, 1547 and 1360 cm$^{-1}$.

UV/VIS (95% EtOH): $\lambda_{max}$=313.0 nm (E=21062); 240.0 nm (E=18068).

EXAMPLE 3

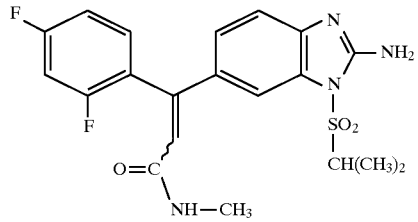

cis

Analysis for $C_{20}H_{20}N_4O_3SF_2$: Calcd: C, 55.29; H, 4.64; N, 12.89; Found: C, 55.29; H, 4.89; N, 12.96.

MS(FD): 434.2 (M⁺).

¹H NMR (300 MHz; d₆-DMSO): δ 1.23 (d, J=7 Hz, 6H); 2.57 (d, J=5 Hz, 3H); 3.83 (septet, J=7 Hz, 1H); 6.17 (s, 1H); 6.82 (d, J=8.1 Hz, 1H); 6.99–7.39 (m, 6H); 7.42 (s, 1H) and 7.98 (d, J=5 Hz, 1H).

IR (KBr): ν 3412, 1662, 1639, 1550, 1445, 1357, 1264 and 1136 cm⁻¹.

UV/VIS (95% EtOH): λ$_{max}$=300.0 nm (E=11944); 252.0 nm (E=20932).

trans

Analysis for C₂₀H₂₀N₄O₃SF₂: Calcd: C, 55.29; H, 4.64; N, 12.89; Found: C, 55.45; H, 4.70; N, 12.77.

MS(FD): 434.2 (M⁺).

¹H NMR (300 MHz; d₆-DMSO): δ 1.22 (d, J=7 Hz, 6H); 2.59 (d, J=5 Hz, 3H); 3.83 (septet, J=7 Hz, 1H); 6.58 (s, 1H); 6.99–7.23 (m, 7H); 7.42 (s, 1H) and 8.08 (d, J=5 Hz, 1H).

IR (KBr): ν 3424, 1664, 1658, 1601, 1553, 1506, 1383, 1229, 1152 and 1138 cm⁻¹.

UV/VIS (95% EtOH): λ$_{max}$=315.0 nm (E=20986); 242.0 nm (E=17916); 214.0 nm (E=29973).

EXAMPLE 4

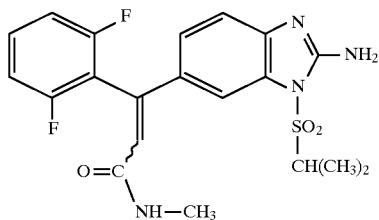

cis

Analysis for C₂₀H₂₀N₄O₃SF₂: Calcd: C, 55.29; H, 4.64; N, 12.89; Found: C, 55.47; H, 4.71; N, 12.84.

MS(FD): 434.2 (M⁺).

¹H NMR (300 MHz; d₆-DMSO): δ 1.22 (d, J=7 Hz, 6H); 2.58 (d, J=5 Hz, 3H); 3.84 (septet, J=7 Hz, 1H); 6.13 (s, 1H); 6.82 (d, J=8 Hz, 1H); 7.01–7.20 (m, 5H); 7.45 (m, 1H); 7.52 (s, 1H); and 8.08 (d, J=5 Hz, 1H).

IR(CHCl₃): ν 1660, 1638, 1606, 1547, 1465, 1359 and 1004 cm⁻¹.

UV/VIS (95% EtOH): λ$_{max}$=307.0 nm (E=13613); 246 nm (E=18327).

trans

Analysis for C₂₀H₂₀N₄O₃SF₂: Calcd: C, 55.29; H, 4.64; N, 12.89; Found: C, 55.04; H, 4.56; N, 12.77.

MS(FD): 434.2 (M⁺).

¹H NMR (300 MHz; d6-DMSO): δ 1.23 (d, J=7 Hz, 6H); 2.58 (d, J=5 Hz, 3H); 3.83 (septet, J=7 Hz, 1H); 6.71 (s, 1H); 7.01–7.19 (m, 5H); 7.21 (d, J=8 Hz, 1H); 7.43 (q, J=8 Hz, 1H); 7.44 (s, 1H); and 8.18 (d, J=5 Hz, 1H).

IR (KBr): ν 3466, 3427, 1662, 1604, 1554, 1464, 1379, 1229, 1174, 1046, 1001 and 687 cm⁻¹.

UV/VIS (95% EtOH): λ$_{max}$=317.0 nm (E=20136); 242.0 nm (E=17889).

The compounds described below were prepared substantially as detailed in Example 1A–E, below, unless otherwise indicated.

EXAMPLE 5

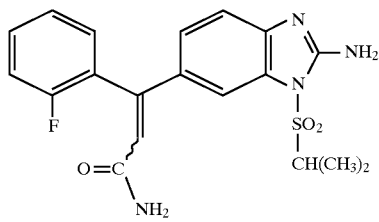

cis

Analysis for C₁₉H₁₉FN₄O₃S: Calcd: C, 56.71; H, 4.76; N, 13.92; Found: C, 56.62; H, 4.60; N, 13.86.

MS(FD): 402.1 (M⁺).

¹H NMR (300 MHz; d₆-DMSO): δ 1.22 (d, J=6.8 Hz, 6H); 3.81 (septet, J=6.8 Hz, 1H); 6.16 (s, 1H); 6.90 (dd, J=8.1,1.2 Hz, 1H); 6.99 (s, 2H); 7.11 (s, 1H); 7.14–7.42 (m, 6H) and 7.47 (s, 1H).

IR (KBr): ν 3438, 3142, 1685, 1654, 1624, 1605, 1554, 1384, 1350, 1297, 1147, 1038 and 764 cm⁻¹.

UV/VIS (95% EtOH): λ$_{max}$=254.0 nm (E=21819)

trans

Analysis for C₁₉H₁₉FN₄O₃S: Calcd: C, 56.71; H, 4.76; N, 13.92; Found: C, 56.90; H, 4.69; N, 13.85.

MS(FD): 402.1 (M⁺).

¹H NMR (300 MHz; d₆-DMSO): δ 1.22 (d, J=6.8 Hz, 6H); 3.82 (septet, J=6.8 Hz, 1H); 6.57 (s, 1H); 6.86 (s, 1H); 7.02–7.22 (m, 7H) and 7.36–7.43 (m, 3H).

IR(KBr): ν 3460, 1678, 1667, 1600, 1552, 1394, 1271 cm⁻¹.

UV/VIS (95% EtOH): λ$_{max}$=285.0 nm (E=3801); 254.0 nm (E=10511); 218.0 nm (E=29782).

EXAMPLE 6

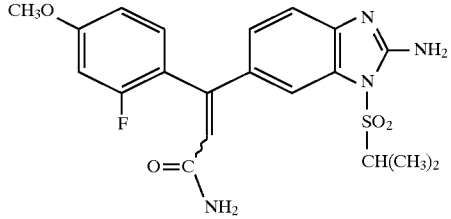

cis

Analysis for C₂₀H₂₁FN₄O₄S: Calcd: C, 55.55; H, 4.89; N, 12.96; Found: C, 55.72; H, 4.89; N, 12.86.

MS(FD): 432.0 (M⁺).

¹H NMR (300 MHz; d₆-DMSO): δ 1.23 (d, J=6.8 Hz, 6H); 3.78 (s, 3H); 3.79 (septet, J=6.8 Hz, 1H); 6.12 (s, 1H); 6.78–6.90 (m, 5H); 6.98 (s, 1H); 7.10 (d, J=2.2 Hz, 1H); 7.12 (d, J=7.8 Hz, 1H); 7.35 (s, 1H) and 7.44 (d, J=1.4 Hz, 1H).

IR (KBr): ν 3443, 3411, 3093, 1659, 1637, 1622, 1611, 1601, 1575, 1565, 1508, 1437, 1394, 1356, 1324, 1278, 1250, 1172, 1153, 1138, 1097, 1040, 1029, 844 and 821 cm⁻¹.

UV/VIS (95% EtOH): λ$_{max}$=285.0 nm (E=18629); 260.0 nm (E=20801).

trans

Analysis for C₂₀H₂₁FN₄O₄S.H₂O: Calcd: C, 53.32; H, 5.15; N, 12.24; Found: C, 53.23; H, 5.11; N, 12.24.

MS(FD) 432.1 (M⁺).

¹H NMR (300 MHz; d₆-DMSO): δ 1.23 (d, J=6.8 Hz, 6H); 3.80 (s, 3H); 3.83 (septet, J=6.8 Hz, 1H); 6.48 (s, 1H); 6.76 (s, 2H); 6.77 (dd, J=20.0, 2.5 Hz, 1H); 6.84 (s, 1H); 7.02 (dd, J=8.7,1.8 Hz, 1H); 7.07 (s, 1H); 7.18 (d, J=8.3 Hz, 1H); 7.37 (s, 2H) and 7.42 (d, J=1.3 Hz, 1H).

IR (CHCl₃): ν 3400, 1661, 1639, 1624, 1603, 1580, 1547, 1508, 1466, 1443, 1386, 1360, 1323, 1291, 1268, 1174, 1156, 1043 and 1033 cm$^{-1}$.

UV/VIS (95% EtOH): $\lambda_{max}$=312.0 nm (E=19477).

EXAMPLE 7

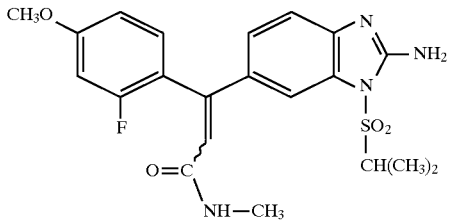

The compound was prepared substantially as detailed in Example 1A–E, using N-methyl-N-trimethylsilylacetamide instead of bis(trimethylsilyl)acetamide.

cis

Analysis for C₂₁H₂₃N₄O₄SF: Calcd: C, 56.59; H, 5.19; N, 12.55; Found: C, 56.42; H, 5.24; N, 12.36.

MS(FD): 446.1 (M⁺).

¹H NMR (300 MHz; d₆-DMSO): δ 1.23 (d, J=6.8 Hz, 6H); 2.56 (d, J=4.5 Hz, 3H); 3.79 (s, 3H); 3.83 (septet, J=6.8 Hz, 1H); 6.10 (s, 1H); 6.86–6.78 (m, 4H); 6.99 (s, 2H); 7.15 (d, J=8.7 Hz, 1H); 7.43 (d, J=1.0 Hz, 1H); 7.93 (d, J=4.5 Hz, 1H).

IR (CHCl₃): ν 3360, 3250, 1638, 1620, 1547, 1507, 1358 and 1157 cm$^{-1}$.

UV/VIS (95% EtOH): $\lambda_{max}$=283.0 nm (E=19090); 259.0 nm (E=21760).

trans

Analysis for C₂₁H₂₃N₄O₄SF: Calcd: C, 56.59; H, 5.19; N, 12.55; Found: C, 56.52; H, 5.20; N, 12.45.

MS(FD): 446 (M⁺).

¹H NMR (300 MHz; d₆-DMSO): δ 1.23 (d, J=6.8 Hz, 6H); 2.56 (d, J=4.6 Hz, 3H); 3.80 (s, 3H); 3.83 (septet, J=6.8 Hz, 1H); 6.46 (s, 1H); 6.76 (s, 1H); 6.77 (dd, J=21.2, 2.4 Hz, 2H); 7.00 (dd, J=8.5,2.0 Hz 1H); 7.07 (s, 2H); 7.17 (d, J=8.5 Hz, 1H); 7.44 (d, J=2.0 Hz, 1H); 7.94 (d, J=4.6 Hz, 1H).

IR (CHCl₃): ν 3510, 3400, 1638, 1603, 1579, 1546, 1508, 1360 and 1156 cm$^{-1}$.

UV/Vis (95% EtOH): $\lambda_{max}$=310.0 nm (E=20794).

EXAMPLE 8

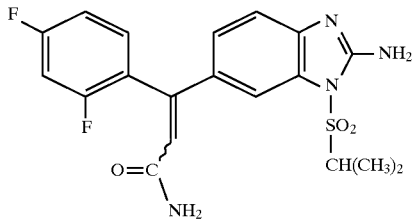

cis

Analysis for C₁₉H₁₈N₄O₃SF₂: Calcd: C, 54.28; H, 4.32; N, 13.33; Found: C, 54.19; H, 4.47; N, 13.53.

¹H NMR (300 MHz, DMSO-d₆): δ 7.47 (d, J=1.3 Hz, 1H); 7.42 (s, 1H); 7.30 (m, 3H); 7.13 (d, J=8.2 Hz, 1H); 7.05 (s, 1H); 7.00 (s, 2H); 6.88 (dd, J=8.4 Hz, 1H); 6.15 (s, 1H); 3.81 (septet, J=6.8 Hz, 1H); 1.23 (d, J=6.8 Hz, 6H).

IR (KBr): 3449, 1655, 1637, 1615, 1595, 1553, 1349, 1264, 1154 and 690 cm$^{-1}$.

MS(FD): 420.1 (M⁺).

UV/Vis (95% EtOH): $\lambda_{max}$=253.0 nm (E=17236).

trans

Analysis for C₁₉H₁₈N₄O₃SF₂.0.5H₂O: Calcd: C, 53.14; H, 4.46; N, 13.05; Found: C, 53.52; H, 4.41; N, 13.05.

¹H NMR (300 MHz, DMSO-d₆): δ 7.48 (s, 1H); 7.40 (d, J=1.4 Hz, 1H); 7.21–7.11 (m, 4H); 7.09 (s, 2H); 7.04 (dd, J=6.8,1.4 Hz, 1H); 6.89 (s, 1H); 6.58 (s, 1H); 3.83 (septet, J=6.8 Hz, 1H); 1.23 (d, J=6.8 Hz, 6H).

IR (KBr): 3470, 3280, 1670, 1651, 1635, 1599, 1589, 1535 and 1394 cm$^{-1}$.

MS(FD): 420 (M⁺).

UV/Vis (95% EtOH): $\lambda_{max}$=316.0 nm (E=19702); 240.0 nm (E=16497).

EXAMPLE 9

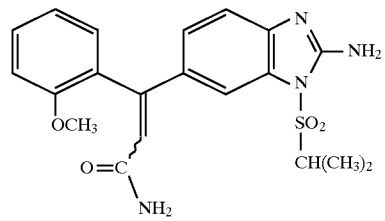

cis not characterized trans

Analysis for C₂₀H₂₂N₄O₄S: Calcd: C, 57.96; H, 5.35; N, 13.52; Found: C, 57.91; H, 5.19; N, 13.35.

¹H NMR (300 MHz, DMSO-d₆) δ 7.37 (s, 1H); 7.31 (m, 1H); 7.14 (d, 1H); 7.10 (s, 1H); 7.02 (m, 5H); 6.95 (m, 1H); 6.73 (s, 1H); 6.44 (s, 1H); 3.79 (septet, 1H); 3.58 (s, 3H); 1.19 (d, 6H).

IR (CHCl₃): 3399, 3009, 1658, 1639 and 1386 cm$^{-1}$.

MS(FD): 414 (M⁺).

UV/Vis (95% EtOH): $\lambda_{max}$=312 nm (E=19305).

EXAMPLE 10

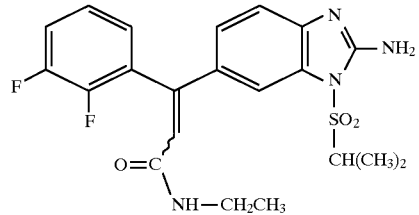

The compound was prepared substantially in accordance with the procedure detailed in Example 1A–E, with the exception that n-butyllithium (15.85 mmol) was slowly added to a solution that was prepared as follows. A cold (-78° C.) solution of lithium bis(trimethylsilyl)amide (15.84 mmol) and N-ethylacetamide (15.85 mmol) in tetrahydrofuran was stirred for 1 hour followed by the addition of chlorotrimethylsilane (15.84 mmol). The resultant solution was stirred for 15 minutes and then allowed to warm slowly to room temperature.

NOTE: The solution was cooled to -78° C. before the addition of the n-butyllithium.

cis

Analysis for C₂₁H₂₂N₄O₃SF₂: Calcd: C, 56.24; H, 4.94; N, 12.49; Found: C, 56.11; H, 5.09; N, 12.24.

¹H NMR (300 MHz, DMSO-d₆): δ 8.05 (t, 1H); 7.35–7.55 (m, 2H); 6.9–7.3 (m, 5H); 6.88 (dd, 1H); 6.18 (s, 1H); 3.85 (septet, 1H); 3.05 (p, 2H); 1.25 (d, 6H); 0.95 (t, 3H).

IR (CHCl$_3$): 2986, 1664, 1602, 1514 and 1482 cm$^{-1}$.
MS(FD): 447.9 (M$^+$).
UV/Vis (95% EtOH): λ$_{max}$=255.0 nm (E=13119.76).
trans;
Analysis for C$_{21}$H$_{22}$N$_4$O$_3$SF$_2$: Calcd: C, 56.24; H, 4.94; N, 12.49; Found: C, 56.46; H, 4.85; N, 12.20.
$^1$H NMR (300 MHz, DMSO-d$_6$): δ 8.10 (t, 1H); 7.25–7.48 (m, 2H); 7.02–7.25 (m, 4H); 6.97 (dd, 1H); 6.86 (t, 1H); 6.57 (s, 1H); 3.81 (septet, 1H); 3.02 (p, 2H); 1.20 (d, 6H); 0.95 (t, 3H).
IR (CHCl$_3$): 3397, 3001, 1639, 1604, 1478, 1359 and 1270 cm$^{-1}$.
MS(FD): 448.1 (M$^+$).
UV/Vis (95% EtOH): λ$_{max}$=316 nm (E=11399.60); 245.00 nm (E=10149.71); 214 nm (E=17027.16).

EXAMPLE 11 cis

Analysis for C$_{18}$H$_{17}$N$_5$O$_3$SF$_2$: Calcd: C, 51.30; H, 4.07; N, 16.62; Found: C, 50.94; H, 4.00; N, 16.63.
$^1$H NMR (300 MHz, DMSO-d$_6$): δ 7.51 (s, 1H); 7.47 (s, 1H); 7.26 (m, 2H); 7.13 (m, 3H); 6.98 (s, 2H); 6.90 (d, 1H); 6.20 (s, 1H); 2.83 (s, 6H).
IR (KBr): 3461, 3438, 1667, 1645, 1384, 1173 and 577 cm$^{-1}$.
MS(FD): 421 (M$^+$).
UV/Vis (95% EtOH): λ$_{max}$=286 nm (E=12460); 256 nm (E=19979.71); 217.5 nm (E=36270.16).
trans Analysis for C$_{18}$H$_{17}$N$_5$O$_3$SF$_2$: Calcd: C, 51.30; H, 4.07; N, 16.62; Found: C, 51.35; H, 4.03; N, 16.68.
$^1$H NMR (300 MHz, DMSO-d$_6$): δ 7.55 (s, 1H); 7.33 (s, 1H); 7.23 (m, 3H); 7.14 (d, 1H); 7.07 (s, 2H); 6.97 (m, 1H); 6.94 (s, 1H); 6.63 (s, 1H); 2.80 (s, 6H).
IR (KBr): 3472, 3448, 3118, 1666, 1557, 1388 and 580 cm$^{-1}$.
MS(FD): 421 (M$^+$).
UV/Vis (95% FtOH): λ$_{max}$=319.5 nm (E=19736); 244 nm (E=15653); 218.5 nm (E=29125).

EXAMPLE 12 cis

Analysis for C$_{19}$H$_{17}$N$_4$O$_3$SF$_3$: Calcd: C, 52.05; H, 3.91; N, 12.77; Found: C, 52.09; H, 3.96; N, 12.61.
$^1$H NMR (300 MHz, DMSO-d$_6$): δ 7.48 (d, J=7.0 Hz, 1H), 7.35 (q, J=9.0 Hz, 1H), 7.15 (d, J=8.2 Hz, 1H), 7.13 (dd, J=8.7,1.8 Hz, 1H), 7.03 (s, 2H), 6.91 (d, J=8.3 Hz, 1H), 6.21 (s, 1H), 3.82 (septet, J=6.8 Hz, 1H), 1.23 (d, J=6.8 Hz, 6H).
IR (CHCl$_3$): 3490, 3360, 1667, 1639, 1607, 1547, 1509, 1474, 1385 and 1357 cm$^{-1}$.
MS(FD): 438.0 (M$^+$).
UV/Vis (95% EtOH): 298.8 nm (E=9947.5); 254.5 nm (E=21502); 212.8 nm (E=36486).
trans Analysis for C$_{19}$H$_{17}$N$_4$O$_3$SF$_3$: Calcd: C, 52.05; H, 3.91; N, 12.77; Found: C, 51.76; H, 4.21; N, 12.47.
$^1$H NMR (300 MHz, DMSO-d$_6$): δ 7.57 (s, 1H), 7.44 (s, 2H), 7.30 (q, J=8.4 Hz, 1H); 7.20 (d, J=8.4 Hz, 1H); 7.12 (s, 2H); 7.03 (dd, J=8.4,1.6 Hz, 1H); 6.97 (s, 1H); 6.64 (s, 1H); 3.86 (septet, J=6.8 Hz, 1H); 1.24 (d, J=6.8 Hz, 6H).
IR (CHCl$_3$): 3399, 1677, 1639, 1603, 1583, 1546, 1510, 1476, 1442, 1388, 1360, 1325, 1273, 1264, 1155 and 1043 cm$^{-1}$.
MS(FD): 438 (M$^+$).
UV/Vis (95% EtOH): λ$_{max}$=319.0 nm (E=27794); 244.0 nm (E=24112).

EXAMPLE 13 cis not characterized trans

Analysis for C$_{19}$H$_{16}$N$_4$O$_3$SF$_4$: Calcd: C, 50.00; H, 3.53; N, 12.28; Found: C, 49.97; H, 3.59; N, 12.03.
$^1$H NMR (300 MHz, DMSO-d$_6$) δ 7.94 (m, 1H); 7.71 (s, 1H); 7.60 (dd, J=5.6,1.6 Hz, 1H); 7.23 (d, J=8.5 Hz, 1H); 7.17–7.06 (m, 3H); 6.95 (d, J=6.8 Hz, 1H); 6.84 (s, 1H); 3.85 (septet, J=6.8 Hz, 1H); 1.25 (d, J=6.8 Hz, 6H).
IR (KBr): 3452, 1679, 1660, 1641, 1638, 1551, 1496, 1399, 1382, 1358, 1270, 1175, 1154, 1044, 936, 687 cm$^{-1}$.
MS(FD): 456.0 (M$^+$).
UV/Vis (95% EtOH): λ$_{max}$=320.0 nm (E=15355) 248.0 nm (E=17540).

EXAMPLE 14

The compound was prepared substantially as detailed in Example 7.

cis

Analysis for C$_{20}$H$_{20}$N$_4$O$_3$SF$_2$: Calcd: C, 55.29; H, 4.64; N, 12.89; Found: C, 55.27; H, 4.67; N, 12.77.

¹H NMR (300 MHz, DMSO-d₆) δ 8.00 (m, 1H); 7.45 (s, 1H); 7.0–7.35 (m, 6H); 6.85 (d, 1H); 6.17 (s, 1H); 3.80 (septet, 1H); 2.57 (d, 3H); 1.20 (d, 6H).

IR (KBr): 3415, 1666, 1551, 1353, 1173 and 1040 cm⁻¹.

MS(FD): 434 (M⁺).

UV/Vis (95% EtOH): λ$_{max}$=254 nm (E=20592); 214.5 nm (E=36320).

trans

Analysis for $C_{20}H_{20}N_4O_3SF_2$: Calcd: C, 55.29; H, 4.64; N, 12.89; Found: C, 55.00; H, 4.56; N, 13.02.

¹H NMR (300 MHz, DMSO-d₆) δ 8.13 (m, 1H); 7.43 (s, 1H); 7.19–7.24 (m, 3H); 7.13 (s, 2H); 6.93–7.05 (m, 2H); 6.6 (s, 1H); 2.58 (d, 3H); 1.22 (d, 6H).

IR (KBr): 3440, 3120, 1664, 1551, 1233 and 1038 cm⁻¹.

MS(FD): 434 (M⁺).

UV/Vis (95% EtOH): λ$_{max}$=316.5 nm (E=20895); 241.5 nm (E=17229); 215.5 nm (31108).

EXAMPLE 15 cis

Analysis for $C_{19}H_{18}N_4O_3SF_2$: Calcd: C, 54.28; H, 4.32; N, 13.33; Found: C, 54.50; H, 4.25; N, 13.14.

¹H NMR (300 MHz, DMSO-d₆) 7.44 (m, 2H); 7.22 (m, 2H); 7.11 (m, 4H); 7.00 (m, 1H); 6.88 (d, 1H); 6.18 (s, 1H); 3.79 (septet, 1H); 1.20 (d, 6H).

¹³C NMR (75 MHz, DMSO-d₆): 166.9, 159.4, 157.3, 156.3, 154.0, 153.4, 142.4, 142.0, 131.6, 130.7, 130.1, 126.1, 125.1, 117.4, 116.5, 115.0, 112.9, 55.5 and 15.5.

IR (KBr): 3441, 3148, 1656, 1486, 1350, 1154, 1037 and 689 cm⁻¹.

MS(FD): 420 (M⁺).

UV/Vis (95% EtOH): λ$_{max}$=256 nm (E=20450); 214.5 nm (E=37022).

trans

Analysis for $C_{19}H_{18}N_4O_3SF_2$: Calcd: C, 54.28; H, 4.32; N, 13.33; Found: C, 54.40; H, 4.34; N, 13.54.

¹H NMR (300 MHz, DMSO-d₆) δ 7.50 (s, 1H); 7.38 (s, 1H); 7.18 (m, 43H); 7.08 (s, 2H); 6.99 (m, 3H); 6.57 (s, 1H); 3.80 (septet, 1H); 1.19 (d, 6H).

¹³C NMR (75 MHz, DMSO-d₆): 165.8, 159.2, 156.9, 156.1, 153.7, 143.4, 142.8, 131.7, 131.5, 129.1, 123.6, 122.1, 117.3, 116.1, 115.7, 115.4, 110.3, 55.8 and 15.6.

IR (KBr): 3163, 1677, 1427, 1269, 1043 and 687 cm⁻¹.

MS(FD): 420 (M⁺).

UV/Vis (95% EtOH): λ$_{max}$=318.5 nm (E=19751); 239.5 nm (E=16318); 215 nm (E=31509).

EXAMPLE 16 cis

Analysis for $C_{19}H_{18}N_4O_3SF_2$: Calcd: C, 54.28; H, 4.31; N, 13.33; Found: C, 54.51; H, 4.56; N, 13.41.

¹H NMR (300 MHz, DMSO-d₆) δ 7.49 (s, 2H); 7.46 (m, 1H); 7.22 (m, 1H); 7.05–7.15 (m, 4H); 7.04 (s, 1H); 6.91 (d, 1H); 6.21 (s, 1H); 3.82 (septet, 1H) and 1.23 (d, J=7 Hz, 6H).

IR (KBr): 3438, 3141, 1685, 1656, 1606, 1477, 1352 and 1275 cm⁻¹.

MS(FD): 420 (M⁺).

UV/Vis (95% EtOH): λ$_{max}$=300 nm (E=10339); 254 nm (E=21435).

trans

Analysis for $C_{19}H_{18}N_4O_3SF_2$: Calcd: C, 54.28; H, 4.32; N, 13.33; Found: C, 54.31; H, 4.37; N, 13.22.

¹H NMR (300 MHz, DMSO-d₆) δ 7.55 (s, 1H); 7.42 (s, 1H); 7.39 (m, 1H); 7.18 (m, 2H); 7.11 (s, 2H); 7.02 (d, 1H); 6.93 (s, 1H); 6.91 (m, 1H); 6.63 (s, 1H); 3.85 (septet, 1H) and 1.21 (d, 6H).

IR (KBr): 2982, 1694, 1659, 1555, 1473, 1349 and 1265 cm⁻¹.

MS(FD): 420 (M⁺).

UV/Vis (95% EtOH): λ$_{max}$=318 nm (E=19511); 241 nm (E=16526).

The compounds in Examples 17 and 18 were prepared substantially as detailed in Example 7.

EXAMPLE 17 cis

Analysis for $C_{20}H_{20}N_4O_3SF_2$: Calcd: C, 55.29; H, 4.64; N, 12.90; Found: C, 55.48; H, 4.54; N, 12.79.

¹H NMR (300 MHz, DMSO-d₆) δ 8.05 (d, J=5 Hz, 1H); 7.58–7.41 (m, 2H); 7.32–7.01 (m, 5H); 6.84 (dd, J=8,1 Hz, 1H); 6.20 (s, 1H); 3.83 (septet, J=7 Hz, 1H); 2.59 (d, J=5 Hz, 3H); 1.23 (d, J=7 Hz, 6H).

IR (CHCl₃): 3450, 2910, 1656, 1638, 1608, 1547, 1479, 1359 and 1273 cm⁻¹.

MS(FD): 434 (M⁺).

UV/Vis (95% EtOH): λ$_{max}$=300.0 nm (E=11012); 254.0 nm (E=22088).

trans

Analysis for $C_{20}H_{20}N_4O_3SF_2$: Calcd: C, 55.29; H, 4.64; N, 12.90; Found: C, 55.53; H, 4.65; N, 12.96.

¹H NMR (300 MHz, DMSO-d₆) δ 8.13 (d, J=5 Hz, 1H); 7.42 (d, J=1 Hz, 1H); 7.40 (q, J=8 Hz, 1H); 7.22–7.13 (m, 4H); 7.05 (dd, J=8,1 Hz, 1H); 6.92 (d, J=8 Hz, 1H); 6.61 (s, 1H); 3.83 (septet, J=7 Hz, 1H); 2.59 (d, J=5 Hz, 3H); 1.25 (d, J=7 Hz, 6H).

IR (CHCl$_3$): 3401, 2992, 1662, 1638, 1603, 1546, 1478, 1359 and 1271 cm$^{-1}$.

MS(FD): 434 (M$^+$).

UV/Vis (95% EtOH): $\lambda_{max}$=316.0 nm (E=19543); 244 nm (E=17677).

EXAMPLE 18

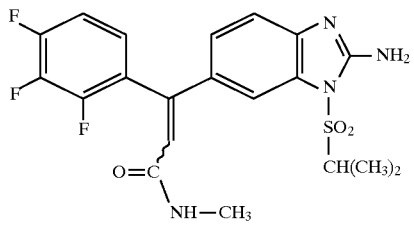

cis

Analysis for C$_{20}$H$_{19}$N$_4$O$_3$SF$_3$: Calcd: C, 53.09; H, 4.23; N, 12.38; Found: C, 52.97; H, 4.38; N, 12.37.

$^1$H NMR (300 MHz, DMSO-d$_6$) δ 8.08 (m, 1H); 7.49 (s, 1H); 7.37 (m, 1H); 6.95–7.20 (m, 4H); 6.87 (d, 1H); 6.19 (s, 1H); 3.84 (septet, 1H); 2.58 (d, 3H) and 1.22 (d, 6H).

IR (CHCl$_3$): 2995, 1656, 1638, 1606, 1509 and 1474 cm$^{-1}$.

MS(FD): 452 (M$^+$).

UV/Vis (95% EtOH): $\lambda_{max}$=311 nm (E=12010); 244 nm (E=19690).

trans

Analysis for C$_{20}$H$_{19}$N$_4$O$_3$SF$_3$: Calcd: C, 53.09; H, 4.23; N, 12.38; Found: C, 53.31; H, 4.29; N, 12.50.

$^1$H NMR (300 MHz, DMSO-d$_6$) δ 8.18 (m, 1H); 7.49 (s, 1H); 7.29 (m, 1H); 7.18 (m, 3H); 6.98 (m, 2H); 6.61 (s, 1H); 3.87 (septet, 1H); 2.58 (d, 3H); 1.23 (d, 6H).

IR (CHCl$_3$): 3022, 1662, 1638, 1604, 1510, 1477 and 1040 cm$^{-1}$.

MS(FD): 452 (M$^+$).

UV/Vis (95% EtOH): $\lambda_{max}$=317 nm (E=20108); 244 nm (E=18099).

The present compounds appear to inhibit replication of plus-strand viral RNA by interfering with the structure and/or function of the viral replication complex (a membrane-bound complex of viral and cellular proteins). Mutant rhinovirus and enterovirus have been isolated which demonstrate very low levels of drug tolerance. These mutants contain a single amino acid substitution in the protein that is expressed by the viral gene known as "3A". Therefore, the compounds of the present invention inhibit the rhinovirus and enterovirus by inhibiting a 3A function. The 3A gene encodes a hydrophobic protein which serves as the scaffolding protein that attaches the proteins of the replication complex to intracellular membranes.

The replicative strategy of flaviviruses such as hepatitis C virus (HCV) and bovine diarrheal virus (BVDVB) is similar to that of the rhinovirus and enterovirus, discussed above. In particular, both families of virus contain single-stranded, messenger-sense RNA that replicates in a cytoplasmic complex via a minus-strand RNA intermediate. In addition, both families of virus translate their genome into a polyprotein that is subsequently cleaved. Furthermore, the replication complexes of both viruses are tightly associated with intracellular membranes. Finally, both families of virus have analogous genomic structures including the presence of a 5' and 3' non-translated region which are required by the viruses for replication. There are two HCV proteins that have been implicated with this intracellular association: NS2 and NS4. It is postulated that either NS2 or NS4 is analogous to the picornavirus 3A protein.

Accordingly, another embodiment of the present invention is a method of treating or preventing a flavivirus infection comprising administering to a host in need thereof an effective amount of a compound of formula I or a pharmaceutically acceptable salt thereof. It is preferred to inhibit hepatitis C.

As noted above, the compounds of the present invention are useful as antiviral agents. They have shown inhibitory activity against various enterovirus and rhinovirus. An embodiment of the present invention is a method of treating or preventing picornaviridae infection comprising administering to a host in need thereof an effective amount of a compound of formula I or a pharmaceutically acceptable salt thereof.

The term "effective amount" as used herein, means an amount of a compound of formula I which is capable of inhibiting viral replication. The picornaviridae inhibition contemplated by the present method includes either therapeutic or prophylactic treatment, as appropriate. The specific dose of compound administered according to this invention to obtain therapeutic or prophylactic effects will, of course, be determined by the particular circumstances surrounding the case, including, for example, the compound administered, the route of administration, the condition being treated and the individual being treated. A typical daily dose will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations are prepared by known procedures using well-known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium); ointments containing, for example, up to 10% by weight of the active compound, soft and hard gelatin capsules, suppositories, sterile injectable solutions, sterile packaged powders and the like.

The following formulation examples are illustrative only and are not intended to limit the scope of the invention in any way. The term "active ingredient" means a compound according to formula I or a pharmaceutically acceptable salt thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active ingredient | 0.25 |
| Methanol | 25.75 |
| Propellant 22 (Chlorodifluoromethane) | 70.00 |
| Total | 100.00 |

The active compound is mixed with ethanol and the mixture added to a portion of the propellant 22, cooled to 30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

|  | Quantity (mg/tablet) |
| --- | --- |
| Active ingredient | 60 |
| Starch | 45 |
| Microcrystalline cellulose | 35 |
| Polyvinylpyrrolidone (as 10% solution in water) | 4 |
| Sodium carboxymethyl starch | 4.5 |
| Magnesium stearate | 0.5 |
| Talc | 1 |
| Total | 150 |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

|  | Quantity (mg/capsule) |
| --- | --- |
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

The following experiment was carried out to demonstrate the ability of the compounds of formula I to inhibit certain virus.

Test Method for Anti-picornaviral Assay

African green monkey kidney cells (BSC-1) or Hela cells (5-3) were grown in 25 cc Falcon flasks at 37° C. in medium 199 with 5 percent inactivated fetal bovine serum (FBS); penicillin (150 units 1 ml) and streptomycin (150 micrograms per milliliter ($\mu$g/ml)). When confluent monolayers were formed, the supernatant growth medium was removed and 0.3 mL of an appropriate dilution of virus (echo, Mengo, Coxsackie, polio or rhinovirus) were added to each flask. After absorption for one hour at room temperature, the virus infected cell sheet was overlaid with a medium comprising one part of 1 percent Ionagar No. 2 and one part double strength Medium 199 with FBS, penicillin and streptomycin which contains drug at concentrations of 100, 50, 25, 12, 6, 3 and 0 $\mu$g/ml. The flask containing no drug served as the control for the test. The stock solutions of vinyl acetylene benzimidazole compounds were diluted with dimethylsulfoxide to a concentration of $10^4$ $\mu$g/ml. The flasks were then incubated for 72 hours at 37° C. for polio, Coxsackie, echo and Mengo virus and 120 hours at 32° C. for rhinovirus. Virus plaques were seen in those areas were the virus infected and reproduced in the cells. A solution of 10 percent formalin and 2 percent sodium acetate was added to each flask to inactivate the virus and fix the cell sheet to the surface of the flask. The virus plaques, irrespective of size, were counted after staining the surrounding cell areas with crystal violet. The plaque count was compared to the control count at each drug concentration. The activity of the test compound was expressed as percentage plaque reduction, or percent inhibition. Alternatively, the drug concentration which inhibits plaque formation by 50 percent can be used as a measure of activity. The 50 percent inhibition is indicated by the symbol IC50.

In vitro CPE/XTT anti-BVDV Assay

MDBK cells were dispersed in the 96-wells microtiter plate at 10,000 cells per well with Minimum Essential Medium containing Earl's balanced salt solution (EBSS), 2% horse serum, penicillin (100 units/ml) and streptomycin (100 $\mu$g/ml). Plates were grown at 37° C. $CO_2$ incubator overnight. The MDBK cells were then infected with ~0.02 moi (multiplicity of infection) of bovine viral diarrhea virus (BVDV, ATCC VR-534). After allowing the virus to adsorb to the cells for 1–2 hours, medium containing serial dilutions of drug or medium alone was added to the wells. After further incubating for 3–4 days (when extensive cpe was apparent in medium alone wells), the antiviral effect of testing drugs were assessed by performing a XTT assay as described below.

XTT [2,3-bis(methoxy-4-nitro-5-sulfophenyl)-2H-tetraazolium-5-carboxanilide, inner salt, sodium salt] at 1 mg/ml for warm medium without FBS were freshly prepared and used immediately. For each 5 ml of the XTT solution, 25 $\mu$l of 5 mM of PMS (phenazine methosulfate) in phosphate buffer saline was added. Then 50 $\mu$l of the freshly prepared XTT/PMS mixture was added to each of the microtiter wells. Incubate at 37° C. ($CO_2$) for 3–4 hours or until color change is prominent. Read absorptance at 450 nm/ref. 650 nm in a spectrophotometer. The concentration of drug required to cause 50% cytotoxic effect as compared to the no drug no virus control ($TC_{50}$) and which to inhibit the development of virus cytopathic effect (cpe) by 50% ($IC_{50}$) was then determined from the liner portion of each dose response curve.

We claim:

1. A compound of the formula I

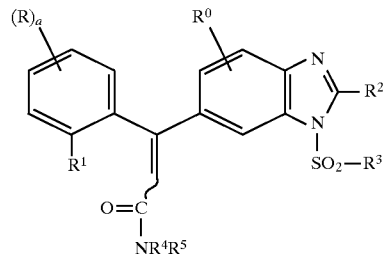

wherein:

a is 1, 2 or 3;

each R is independently halo, cyano, amino, halo($C_1$–$C_4$) alkyl, di($C_1$–$C_4$)alkylamino, azido, $C_1$–$C_6$ alkyl, carbamoyl, carbamoyloxy, carbamoylamino, $C_1$–$C_4$ alkoxy, $C_1$–$C_4$ alkylthio, $C_1$–$C_4$ alkylsulfinyl, $C_1$–$C_4$ alkylsulfonyl, pyrrolidino, piperidino or morpholino;

$R^0$ is hydrogen, halo, $C_1$–$C_4$ alkyl or $C_1$–$C_4$ alkoxy;

$R^1$ is halo, cyano, hydroxy, methyl, ethyl, methoxy, ethoxy, methylthio, methylsulfinyl or methylsulfonyl;

$R^2$ is hydrogen, amino or —NHC(O)($C_1$–$C_6$ alkyl);

$R^3$ is dimethylamino, $C_1$–$C_{10}$ alkyl, halo($C_1$–$C_6$)alkyl, $C_3$–$C_7$ cycloalkyl, substituted $C_3$–$C_7$ cycloalkyl, phenyl, substituted phenyl, naphthyl, thienyl, thiazolidinyl, furyl, pyrrolidino, piperidino, morpholino or a group of the formula:

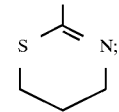

$R^4$ and $R^5$ are independently hydrogen or $C_1$–$C_4$ alkyl;

or a pharmaceutically acceptable salt thereof.

2. A compound according to claim 1 where:

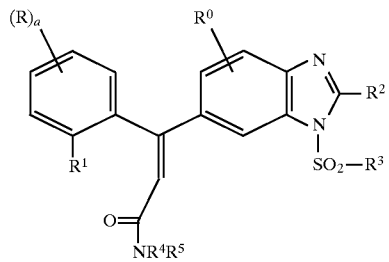

where:

a is 1 or 2;

each R is independently halo, $C_1$–$C_4$ alkyl, $C_1$–$C_4$ alkoxy or di($C_1$–$C_4$)alkylamino;

$R^0$ is hydrogen;

$R^2$ is amino;

$R^3$ is dimethylamino, $C_1$–$C_6$ alkyl, halo($C_1$–$C_6$)alkyl, $C_3$–$C_7$ cycloalkyl, substituted $C_3$–$C_7$ cycloalkyl, thienyl, thiazolidinyl, pyrrolidino, piperidino or morpholino;

$R^4$ is hydrogen, methyl or ethyl;

$R^5$ is hydrogen, methyl or ethyl;

or a pharmaceutically acceptable salt thereof.

3. A compound according to claim 2 where:

a is 1;

each R is independently fluoro, methyl, ethyl, methoxy, ethoxy, dimethylamino;

$R^0$ is hydrogen;

$R^3$ is dimethylamino, $C_1$–$C_4$ alkyl, $C_3$–$C_7$ cycloalkyl or pyrrolidino;

or a pharmaceutically acceptable salt thereof.

4. A compound according to claim 3 which is:

or a pharmaceutically acceptable salt thereof.

5. A pharmaceutical formulation comprising a compound of claim 1, or a pharmaceutically acceptable salt thereof, in combination with a pharmaceutically acceptable carrier, diluent or excipient therefor.

6. A pharmaceutical formulation according to claim 5 where the compound is one where:

[Structure: general formula with substituents (R)ₐ, R⁰, R¹, R², R³, NR⁴R⁵]

where:
a is 1 or 2;
each R is independently halo, $C_1$–$C_4$ alkyl, $C_1$–$C_4$ alkoxy or di($C_1$–$C_4$)alkylamino;
$R^0$ is hydrogen;
$R^2$ is amino;
$R^3$ is dimethylamino, $C_1$–$C_6$ alkyl, halo($C_1$–$C_6$)alkyl, $C_3$–$C_7$ cycloalkyl, substituted $C_3$–$C_7$ cycloalkyl, thienyl, thiazolidinyl, pyrrolidino, piperidino or morpholino;
$R^4$ is hydrogen, methyl or ethyl;
$R^5$ is hydrogen, methyl or ethyl;
or a pharmaceutically acceptable salt thereof.

7. A pharmaceutical formulation according to claim 6 where the compound is one where:
a is 1;
each R is independently fluoro, methyl, ethyl, methoxy, ethoxy, dimethylamino;
$R^0$ is hydrogen;
$R^3$ is dimethylamino, $C_1$–$C_4$ alkyl, $C_3$–$C_7$ cycloalkyl or pyrrolidino;
or a pharmaceutically acceptable salt thereof.

8. A pharmaceutical formulation according to claim 7 where the compound is one where:

[Several chemical structures of benzimidazole-based compounds with various fluorophenyl and methoxyphenyl substituents]

or a pharmaceutically acceptable salt thereof.

9. A method for inhibiting a picornavirus comprising administering to a host in need thereof, an effective amount of a compound of claim 1, or a pharmaceutically acceptable salt thereof.

10. A method according to claim 9 where the compound is one where:

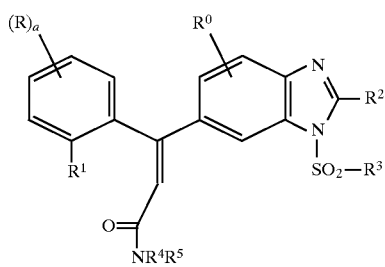

where:
  a is 1 or 2;
  each R is independently halo, $C_1$–$C_4$ alkyl, $C_1$–$C_4$ alkoxy or di($C_1$–$C_4$)alkylamino;
  $R^0$ is hydrogen;
  $R^2$ is amino;
  $R^3$ is dimethylamino, $C_1$–$C_6$ alkyl, halo($C_1$–$C_6$)alkyl, $C_3$–$C_7$ cycloalkyl, substituted $C_3$–$C_7$ cycloalkyl, thienyl, thiazolidinyl, pyrrolidino, piperidino or morpholino;
  $R^4$ is hydrogen, methyl or ethyl;
  $R^5$ is hydrogen, methyl or ethyl;
or a pharmaceutically acceptable salt thereof.

11. A method according to claim 10 where the compound is one where:
  a is 1;
  each R is independently fluoro, methyl, ethyl, methoxy, ethoxy, dimethylamino;
  $R^0$ is hydrogen;
  $R^3$ is dimethylamino, $C_1$–$C_4$ alkyl, $C_3$–$C_7$ cycloalkyl or pyrrolidino;
or a pharmaceutically acceptable salt thereof.

12. A method according to claim 11 where the compound is one where:

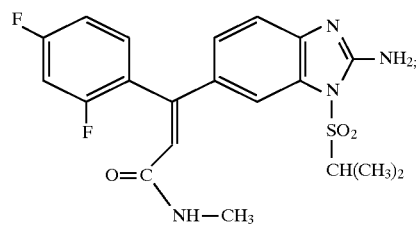

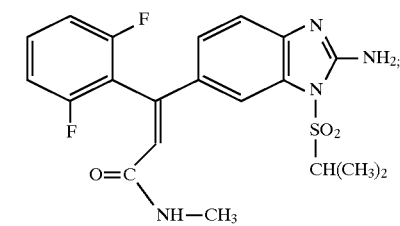

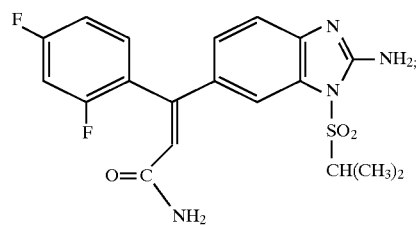

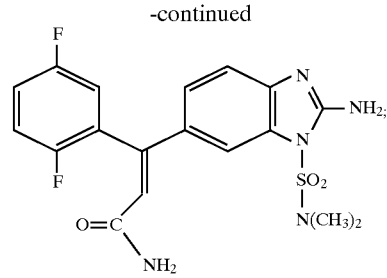

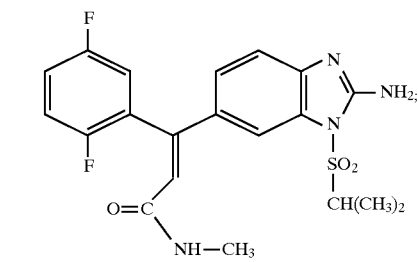

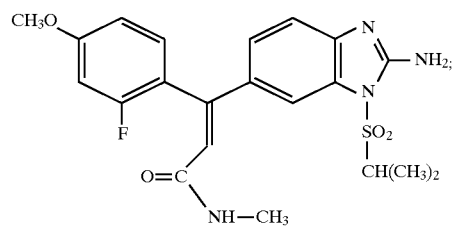

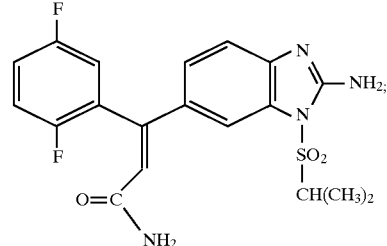

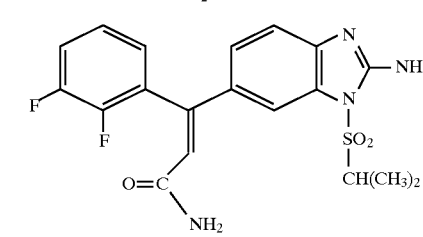

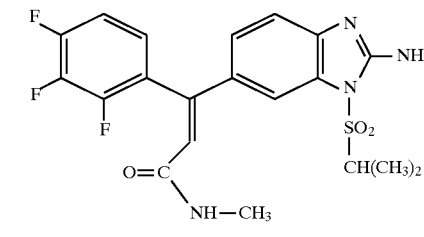

or a pharmaceutically acceptable salt thereof.

13. A method according to claim 9 where the picornavirus is a rhinovirus.

14. A method according to claim 9 where the picornavirus is an enterovirus.

* * * * *